US 8,535,741 B2
Sep. 17, 2013

(12) United States Patent
Zhou et al.

(10) Patent No.: US 8,535,741 B2
(45) Date of Patent: Sep. 17, 2013

(54) METHOD AND COMPOSITION FOR ADMINISTERING BIOACTIVE COMPOUNDS DERIVED FROM *MORINDA CITRIFOLIA*

(75) Inventors: Bing-Nan Zhou, Shanghai (CN); Chen Su, West Jordan, UT (US); Afa K. Palu, American Fork, UT (US); Brett J. West, Cedar Hills, UT (US); Shixin Deng, Lehi, UT (US); Claude Jarakae Jensen, Cedar Hills, UT (US); Stephen Story, Alpine, UT (US)

(73) Assignee: Morinda, Inc., Provo, UT (US)

( * ) Notice: Subject to any disclaimer, the term of this patent is extended or adjusted under 35 U.S.C. 154(b) by 0 days.

(21) Appl. No.: 13/246,619

(22) Filed: Sep. 27, 2011

(65) Prior Publication Data

US 2013/0079380 A1    Mar. 28, 2013

Related U.S. Application Data

(62) Division of application No. 11/746,798, filed on May 10, 2007, now Pat. No. 8,025,910.

(60) Provisional application No. 60/799,793, filed on May 12, 2006.

(51) Int. Cl.
*A61K 36/746* (2006.01)
*A61K 36/00* (2006.01)

(52) U.S. Cl.
USPC .......................................... 424/777; 424/725

(58) Field of Classification Search
USPC ........................................ 424/725, 774, 777
See application file for complete search history.

(56) References Cited

U.S. PATENT DOCUMENTS

| | | |
|---|---|---|
| 4,039,559 A | 8/1977 | Nakamura |
| 4,409,144 A | 10/1983 | Heinicke |
| 4,463,025 A | 7/1984 | Strobel |
| 4,543,212 A | 9/1985 | Heinicke |
| 4,666,606 A | 5/1987 | Heinicke |
| 4,708,964 A | 11/1987 | Allen |
| 4,793,991 A | 12/1988 | Slimak |
| 4,948,785 A | 8/1990 | Nguyen |
| 4,996,051 A | 2/1991 | Meer et al. |
| 5,071,878 A | 12/1991 | Herschler |
| 5,106,634 A | 4/1992 | Thacker et al. |
| 5,110,803 A | 5/1992 | Nguyen |
| 5,213,836 A | 5/1993 | McGillivray et al. |
| 5,268,467 A | 12/1993 | Verbiscar |
| 5,275,834 A | 1/1994 | Thibault et al. |
| 5,288,491 A | 2/1994 | Moniz |
| 5,431,927 A | 7/1995 | Hand et al. |
| 5,472,699 A | 12/1995 | Duffy et al. |
| 5,503,825 A | 4/1996 | Lane |
| 5,565,435 A | 10/1996 | Yoneyama |
| 5,595,756 A | 1/1997 | Baily et al. |
| 5,616,569 A | 4/1997 | Reinhart |
| 5,717,860 A | 2/1998 | Graber et al. |
| 5,725,875 A | 3/1998 | Noll et al. |
| 5,731,356 A | 3/1998 | Jones et al. |
| 5,736,174 A | 4/1998 | Cooper et al. |
| 5,744,187 A | 4/1998 | Gaynor |
| 5,770,217 A | 6/1998 | Kutilek, III et al. |
| 5,776,441 A | 7/1998 | Scancarella et al. |
| 5,843,499 A | 12/1998 | Moreau et al. |
| 5,851,573 A | 12/1998 | Lepine et al. |
| 5,922,766 A | 7/1999 | Acosta et al. |
| 5,961,998 A | 10/1999 | Arnaud et al. |
| 5,962,043 A | 10/1999 | Jones et al. |
| 5,976,549 A | 11/1999 | Lewandowski |
| 6,029,141 A | 2/2000 | Bezos et al. |
| 6,039,952 A | 3/2000 | Sunvold et al. |
| 6,086,859 A | 7/2000 | Calello et al. |
| 6,086,910 A | 7/2000 | Howard et al. |
| 6,133,323 A | 10/2000 | Hayek |
| 6,136,301 A | 10/2000 | Pelle et al. |
| 6,139,897 A | 10/2000 | Goto et al. |
| 6,156,355 A | 12/2000 | Shields, Jr. et al. |
| 6,214,351 B1 | 4/2001 | Wadsworth et al. |
| D445,696 S | 7/2001 | Matauch |
| 6,254,913 B1 | 7/2001 | Wadsworth et al. |
| 6,261,566 B1 | 7/2001 | Pillai et al. |

(Continued)

FOREIGN PATENT DOCUMENTS

| | | |
|---|---|---|
| CN | 1101256 | 4/1995 |
| EP | 0555573 A1 | 8/1993 |

(Continued)

OTHER PUBLICATIONS

Daulataba et al., "Ricinoleic acid in *Morinda citrifolia* seed oil," J. Oil Tech. Assoc. India (Mumbai, India) 21(2):26-27 (1989).
Dittmar, Morinda, "Use in Indigenous Samoan Medicine," J. of Herbs, Spices & Medicinal Plants, 1(3):77-92 (1993).
El-Gammal et al., "Antimicrobial Activities of Some Flavonoid Compounds," Microbiol. 141:561-565 (1986).
Elkins, Hawaiian Noni, Woodland Publishing, pp. 6-31 (1998).
Farine et al., "Volatile Components of Ripe Fruits of *Morinda citrifolia* and Their Effects on *Drosophila*", Phytochemistry, 1996, pp. 433-438, vol. 41, No. 2.
Fisher, Living Better, V 1(5).
Gagnon, D., "Liquid Herbal Drops in Everyday Use," 3d Ed., Bot. Res. Ed. Inst., p. 27 (1997).
Gura, "Systems for Identifying New Drugs are Often Faulty," Science 278:1041-1042 (1997).
Hirazumi et al., "An Immunomodulatory Polysaccharide-Rich Substance from the Fruit Juice of *Morina citrifolia*(Noni) with Antitumor Activity,"Phytotherapy Research, 13:380-387(1999).

(Continued)

*Primary Examiner* — My-Chau T Tran
(74) *Attorney, Agent, or Firm* — Kirton McConkie; Michael F. Krieger

(57) ABSTRACT

This invention relates to a method and composition for providing in various health benefits by administering various bioactive compounds derived from the plant *Morinda cirtrifolia* to individuals. This invention relates to using one or more of the following: Noni Leaf Extract; Noni Leaf Juice; and/or Roast Leaf More particularly this invention relates to administering one or more of the following: Pyro-phorbide a, Pheophorbide a, Purpin 7, and/or Pheophorbide all which may be derived from Noni leaf extract, Noni leaf juice, and/or Roast leaf Moreover, the foregoing formulations result in alleviating pain and inflammation.

15 Claims, 2 Drawing Sheets

(56) References Cited

U.S. PATENT DOCUMENTS

| | | |
|---|---|---|
| 6,280,751 B1 | 8/2001 | Fletcher et al. |
| 6,291,533 B1 | 9/2001 | Fleischner |
| 6,299,925 B1 | 10/2001 | Xiong et al. |
| 6,387,370 B1 | 5/2002 | Yegorva |
| 6,405,948 B1 | 6/2002 | Hahn et al. |
| 6,528,106 B2 | 3/2003 | Wadsworth et al. |
| 6,589,514 B2 | 7/2003 | Jensen et al. |
| 6,737,089 B2 | 5/2004 | Wadsworth et al. |
| 6,749,875 B2 | 6/2004 | Selleck |
| 6,855,345 B2 | 2/2005 | Jensen et al. |
| 6,855,354 B2 | 2/2005 | Jensen et al. |
| 7,014,873 B2 | 3/2006 | West et al. |
| 7,018,662 B2 | 3/2006 | Jensen et al. |
| 7,033,624 B2 | 4/2006 | Jensen et al. |
| 7,048,952 B2 | 5/2006 | Gerson et al. |
| 7,070,813 B2 | 7/2006 | Jensen et al. |
| 7,122,211 B2 | 10/2006 | Jensen et al. |
| 7,144,439 B2 | 12/2006 | Isami |
| 7,186,422 B2 | 3/2007 | Jensen et al. |
| 7,244,463 B2 | 7/2007 | Wadsworth |
| 7,264,829 B2 | 9/2007 | Zhou |
| 7,442,395 B2 | 10/2008 | West |
| 8,025,910 B2 * | 9/2011 | Zhou et al. .................... 424/777 |
| 2001/0033871 A1 | 10/2001 | Gidlund |
| 2002/0068102 A1 | 6/2002 | Su et al. |
| 2002/0090406 A1 | 7/2002 | Su et al. |
| 2002/0187168 A1 | 12/2002 | Jensen et al. |
| 2003/0060405 A1 | 3/2003 | Klieiman et al. |
| 2003/0086990 A1 | 5/2003 | Wang et al. |
| 2003/0108629 A1 | 6/2003 | Chou |
| 2003/0108630 A1 | 6/2003 | Story et al. |
| 2003/0108631 A1 | 6/2003 | Jensen et al. |
| 2003/0134001 A1 | 7/2003 | Jensen et al. |
| 2003/0134002 A1 | 7/2003 | Jensen et al. |
| 2003/0157205 A1 | 8/2003 | Jensen et al. |
| 2003/0206895 A1 | 11/2003 | Cavazza |
| 2003/0225005 A1 | 12/2003 | Gerson et al. |
| 2004/0086583 A1 | 5/2004 | Jensen et al. |
| 2004/0191341 A1 | 9/2004 | Palu et al. |
| 2004/0192761 A1 | 9/2004 | Palu et al. |
| 2004/0213862 A1 | 10/2004 | Su et al. |
| 2004/0224038 A1 | 11/2004 | Wang et al. |
| 2004/0244447 A1 | 12/2004 | Isami |
| 2004/0258780 A1 | 12/2004 | Woltering et al. |
| 2005/0037101 A1 | 2/2005 | Wang et al. |
| 2005/0075925 A1 | 4/2005 | Sash |
| 2005/0084551 A1 | 4/2005 | Jensen et al. |
| 2005/0106275 A1 | 5/2005 | Su et al. |
| 2005/0118291 A1 | 6/2005 | Wang et al. |
| 2005/0147700 A1 | 7/2005 | Jensen et al. |
| 2005/0158412 A1 | 7/2005 | Su et al. |
| 2005/0181082 A1 | 8/2005 | Isami et al. |
| 2005/0186296 A1 | 8/2005 | Palu et al. |
| 2005/0196476 A1 | 9/2005 | Zhou et al. |
| 2005/0202108 A1 | 9/2005 | Palu et al. |
| 2005/0202109 A1 | 9/2005 | Palu et al. |
| 2005/0260291 A1 | 11/2005 | Palu et al. |
| 2006/0088611 A1 | 4/2006 | Wang et al. |
| 2006/0141076 A1 | 6/2006 | Palu et al. |
| 2006/0159788 A1 | 7/2006 | West et al. |
| 2006/0193932 A1 | 8/2006 | Jensen et al. |
| 2006/0269630 A1 | 11/2006 | Palu et al. |
| 2006/0269631 A1 | 11/2006 | Su et al. |
| 2006/0275359 A1 | 12/2006 | Jensen et al. |
| 2006/0280818 A1 | 12/2006 | Palu et al. |
| 2007/0087066 A1 | 4/2007 | Gerson et al. |
| 2007/0154580 A1 | 7/2007 | Palu |
| 2007/0166417 A1 | 7/2007 | Palu |
| 2007/0196524 A1 | 8/2007 | Isami |
| 2007/0202206 A1 | 8/2007 | Palu |
| 2007/0237848 A1 * | 10/2007 | Rawson et al. ............... 424/776 |
| 2007/0286910 A1 | 12/2007 | Zhou |
| 2007/0298142 A1 * | 12/2007 | Godbee et al. .................... 426/2 |
| 2009/0053336 A1 | 2/2009 | West |
| 2009/0068204 A1 | 3/2009 | Darien |
| 2010/0215786 A9 | 8/2010 | Jensen |
| 2011/0160057 A1 | 6/2011 | Wadsworth |
| 2011/0171333 A1 | 7/2011 | Wadsworth |

FOREIGN PATENT DOCUMENTS

| | | |
|---|---|---|
| EP | 0710450 A1 | 5/1996 |
| FR | 2673639 | 9/1992 |
| FR | 2783137 | 3/2000 |
| GB | 2253984 A | 9/1992 |
| JP | 355064504 | 5/1980 |
| JP | 61185167 | 8/1986 |
| JP | 62132829 | 6/1987 |
| JP | 06087736 | 3/1994 |
| JP | 06087737 | 3/1994 |
| JP | 8-208501 | 8/1996 |
| JP | 08208461 | 8/1996 |
| JP | 9-110688 | 4/1997 |
| JP | 11-43442 A | 2/1999 |
| JP | 2000095663 | 4/2000 |
| WO | 88/05304 A1 | 7/1988 |
| WO | 01/15551 A1 | 3/2001 |
| WO | 01/15553 A1 | 3/2001 |
| WO | 01/64231 A1 | 9/2001 |
| WO | 02/45654 A2 | 6/2002 |
| WO | 02/45734 A1 | 6/2002 |

OTHER PUBLICATIONS

Lampur, "*Morinda* achieves phenomenal sales of Tahitian noni juice", Malayasian Nat. News Agency Jul. 1999, p. 1.
Peres et al., "Tetraoxygenated naturally occurring xanthones," Phytochemestry 55:683-710 (2000).
Product Alert. Oct. 11, 1999 29(19) PROMT Abstract.
Product Alert. Dec. 27, 1999 (29(24) PROMT Abstract.
Product Alert. Jun. 12, 2000 30(11) PROMT Abstract.
Rosenfeld, "Tropical Noni, a Tonic Boom; Nasty-Tasting Fruit Rockets onto the Health Product Market," Wash. Post; Aug. 7, 1997, p. C01:1-4 of Proquest.
Sang et al.,"Chemical Components in Noni Fruits and Leaves (*Morinda citrifolia* L.); Quality Management of Nutraceuticals,"Proceedings of Symposium,ACS,Wash.,DC pp:134-150(2002.
Sang et al., "Flavonal Glycosides and Novel Irdoid Glycoside from the Leaves of *Morinda citrifolia*," J. Agric.
"Rachel Perry Environmental Skin Protector SPF 18," Product Alert, V.29(2) (1999).
Tahitian Noni Products (http://www.noni-now.com) (1998-2003).
Wang et al., "Novel Trisaccharide Fatty Acid Ester Identified from the Fruits of *Morinda citrifolia* (Noni)" J. Agric. Food Chem. 47(12):4880-7882 (1999).
Wang, Mingfu., "Chemical Components of Sage, Thyme and noni and their antioxidant and anticancer activities,".
Webb, "Noni Juice Advice," Prevention Magazine 52:66 (2000).
Website publication: "A Pure Hawaiian Noni Juice," web.archive. org/web/20030523122956/http://www.nonialoha.com (2003).
Website publication: "Betterman" by Interceuticals, www. naturalhealtheconsultant.com/Monographs/Betterman.html (1998).
Website publication: "*Morinda*," www.drugdigest.org/DD/DV/HebsTake/0,3927,552025/Morinda.00.html (2003).
Website publication: "NONI in the News," www.incc.org/news-june. htm (2002).
Website publication: "NONI: Ugly but with a beautiful soul," www. web.archive.org/web/20020207214423/http://wwwInukahivatrading.com/noni.htm (2002).
Website publication: "Noni Juice," www.tipsofallsorts.com/noni. html p. 1-11 (1999).
Website publication "Noni or Nonu Fruit," www.noni-nonu.com (1999).
Website publication "100% Pure Standardized Noni Juice," www. evitamins.com (1999).
Weil, A., "Alternatives," Northern Echo, Darlington, UK, p. 1-2 (2000).
Younos et al., "Analgesic and Behavioural Effects of *Morinda-citrifolia*" Planta Medica 56(5):430-434 (1990).
Bennett et al., "Xanthones from Guttiferae" Phytochemistry vol. 28, No. 4, pp. 967-998 (1989).

Brock et al., "Biology of Microorganisms," 6th Ed. Prentice-Hall, Inc. p. 334 (1994).

Conquer et al., "Supplementation with quercetin markedly increases plasma quercetin concentration . . . " Journal of Nutrition, vol. 128, Iss. 3, pp. 593-597 (Mar. 1998).

Csiszar et al., "Extracts of *Morinda* . . . Exhibit Selective Anti-Tumor . . . " (Abstract) Proceedings of the American Association for Cancer Research, vol. 42 p. 634 (Mar. 2001).

Cushman et al. "Angiotensin Converting Enzyme Inhibitors: Evolution . . . " Angiotensin Converting Enzyme Inhibitors, Horovitz Ed., pp. 3-25, Urban & Schwarzenberg (1981).

Lee, "MorindaNet plans for e-commerce" New Straits Times, beginning p. 7, (Jun. 17, 1999).

"Angiotensin I-Converting Enzyme; ACE" Online Mendelian Inhereitance in Man, Johns Hopkins University Website Publication, (Mar. 3, 2004).

Singh et al., "Folk Medicine in Tonga: A Study on the Use of Herbal Medicines . . . " Journal of Ethnopharmacology 12 (1984) pp. 305-329.

Wang et al. "Cancer Preventive Effect of *Morinda citrifolia* (Noni)" Annals of the N.Y. Academy of Sciences pp. 161-168 (2001) 952.

Website publication "Tahitian Noni Skin Care Systems," www.nonidrink.com/skin_care.html (2002).

Website publication "Nature's Sunshine Products," wwww.synergeyworldwide.com/SG/products/productlines/products.aspx?product=SG4066 (Feb. 24, 2005).

Bain, J. "Secret World of Noni," Toronto Star, Toronto, Ontario: Aug. 6, 1999, p. 1 (pp. 1-5 of ProQuest).

Navarre, I "76 Ways to Use Noni Fruit Juice for your Better Health" Pride Publishing, Orem, Utah, (Apr. 2001), pp. 57-59, 81-83, and 119-124.

Cimanga et al., Flavonoids O-glycosides from Leaves of *Morinda morindoides*, Phytochemistry, 1995, 38(5), pp. 1301-1303.

Website Publication, Indo World, Nature'salternative.com, (Jan. 1, 2001), http://www.indo-world.com/profile.htm.

Website Publication, Nature'salternative.com, http://www.naturesalternatives.supplements/noni.html, NutriScience Innovation, http://www.nutriscience.usea.com/productinfo.htm.

Website Publication, National Cancer Institute, http:/www.cancer.gov,/Templates/drugdictionary.aspx?CdrID=304320 CAT.INST, http://cat.inst.fr/?aModele=afficheNcpsidt=4257124.

Chye, K.T., "A Juice for Many Ailments," New Straits Times, Aug. 10, 1999, pp. 5 (pp. 1-3 of ProQuest direct).

Sang et al., Analysis of chemical components in noni fruits (*Morinda citrifolia*), PTO-892.

Blanco et al. "The noni fruit (*Morinda citrifolia* L.): A review of agricultural research, nutritional and therapeutic properties," Journal of Food Composition and Analysis, 2006, vol. 19, pp. 645-654.

\* cited by examiner

METHOD AND COMPOSITION FOR ADMINISTERING BIOACTIVE COMPOUNDS DERIVED FROM *MORINDA CITRIFOLIA*

RELATED APPLICATIONS

This application claims priority to U.S. Patent Application Ser. No. 60/799,793, filed May 12, 2006 and entitled "Method and Composition for Administering Bioactive Compounds Derived from Morinda Citrifolia" and is a divisional application claiming priority to U.S. patent application Ser. No. 11/746,798 filed May 10, 2007, now U.S. Pat. No. 8,025,910 entitled "Method and Compositions for Administering Bioactive Compounds Derived From Morinda Citrifolia."

BACKGROUND

1. Field of Invention

This invention relates to a method and composition for providing in various health benefits by administering various bioactive compounds derived from the plant *Morinda cirtrifolia* to individuals. More particularly this invention relates to administering one or more of the following: Pyro-phorbide a, Pheophorbide a, Purpin 7, and/or Pheophorbide Phypolesper all which may be derived from Noni leaf extract, Noni leaf juice, and/or Roast leaf. Moreover, the foregoing formulations result in alleviating pain and inflammation.

2. Background

People are becoming increasingly more conscientious of their health. With a variety of deadly diseases and ailments threatening the public health each year, efforts to find treatments and medications that treat and prevent disease are ongoing. Moreover, studies show that comprehensive, novel early prevention and detection strategies increase healthy life potential.

SUMMARY AND OBJECTS OF THE INVENTION

Some embodiments of this invention relate to methods and compositions for providing various health benefits by administering bioactive compounds derived from the plant *Morinda cirtrifolia* to individuals.

Some embodiments relate to using one or more of the following: Noni Leaf Extract; Noni Leaf Juice; and/or Roast Leaf to inhibit the following: HMG-CoA Reductase; Phosphodiesterases (3 and 4) PDE3 and PDE4; 5-Lipoxygenase (LOX) and 15-LOX; Xanthine Oxidase (X0); Gamma Amino Butyric Acid (GABA) and the growth of the second most common human skin cancer cell line.

Some embodiments relate to administering one or more of the following: Pyro-phorbide a, Pheophorbide a, Purpin 7, and/or Pheophorbide Phypolesper all which may be derived from Noni leaf extract, Noni leaf juice, and/or Roast leaf.

Some embodiments result in alleviating pain and inflammation.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
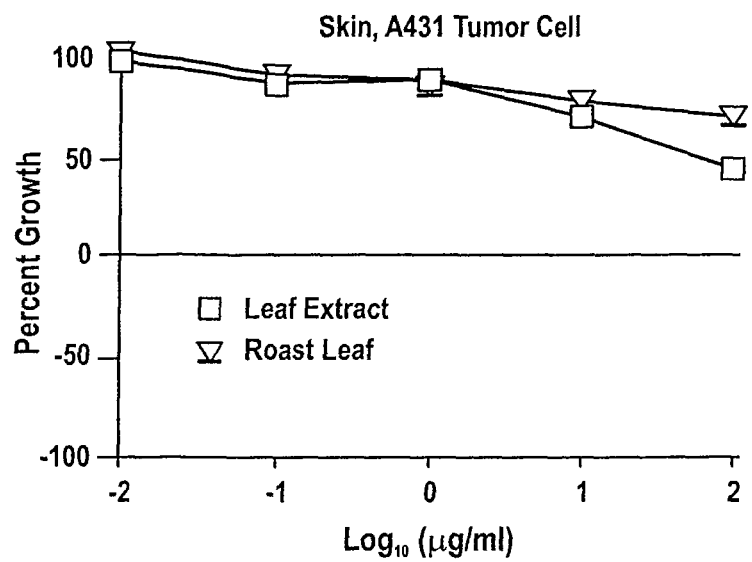
FIG. 1 shows an example of a concentration-response curve for inhibition of growth in A431 human tumor cell line treated with Leaf Extract.
Figure 2:
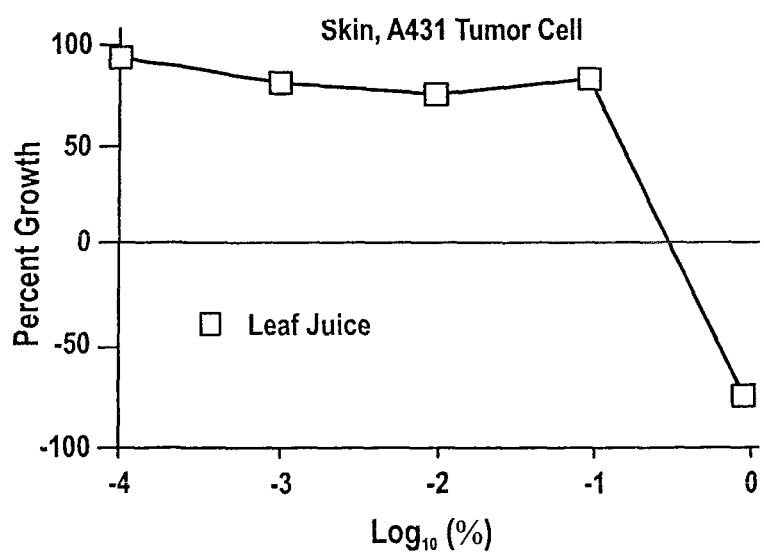
FIG. 2 shows an example of a concentration-response curve for inhibition of growth in A431 human tumor cell line treated with Leaf Juice.
Figure 3:
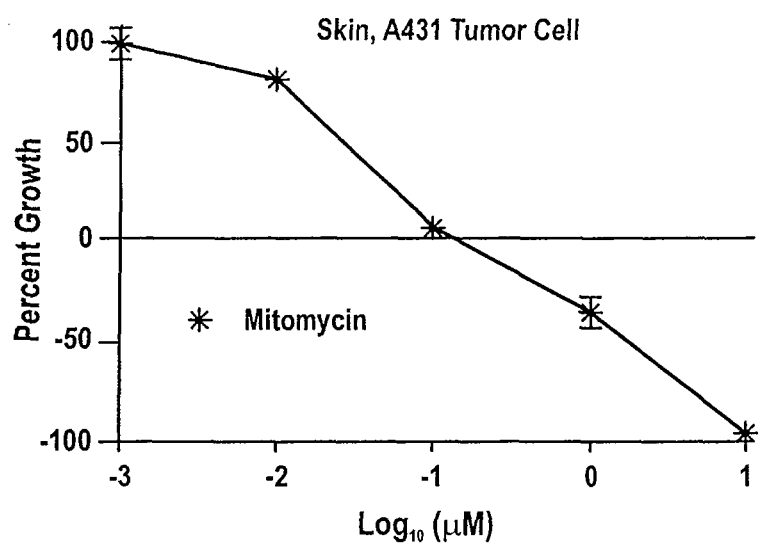
FIG. 3 shows an example of a concentration-response curve for inhibition of growth in A431 human tumor cell line treated with Leaf Roast.

It will be readily understood that the components of the present invention, as generally described herein, could be arranged and designed in a wide variety of different configurations. Thus, the following more detailed description of embodiments of the compositions and methods of the present invention is not intended to limit the scope of the invention, as claimed, but is merely representative of the presently preferred embodiments of the invention. The scope of the invention is, therefore, indicated by the appended claims rather than by the foregoing description. All changes that come within the meaning and range of equivalency of the claims are to be embraced within their scope.

This invention relates to a method and composition for providing in various health benefits by administering various bioactive compounds derived from the plant *Morinda cirtrifolia* to individuals. This invention relates to using one or more of the following: Noni Leaf Extract; Noni Leaf Juice; and/or Roast Leaf to inhibit the following: HMG-CoA Reductase; Phosphodiesterases (3 and 4) PDE3 and PDE4; 5-Lipoxygenase (LOX) and 15-LOX; Xanthine Oxidase (X0); Gamma Amino Butyric Acid (GABA) and the growth of the second most common human skin cancer cell line. More particularly this invention relates to administering one or more of the following: Pyro-phorbide a, Pheophorbide a, Purpin 7, and/or Pheophorbide Phypolesper all which may be derived from Noni leaf extract, Noni leaf juice, and/or Roast leaf. Moreover, the foregoing formulations result in alleviating pain and inflammation.

General Description of the *Morinda citrifolia* L. Plant

The Indian Mulberry or *Morinda citrifolia* plant, known scientifically as *Morinda Citrifolia* L. ("*Morinda citrifolia*"), is a shrub or small tree up to 10 m in height. The leaves are oppositely arranged with an elliptic to ovate form. The small white flowers are contained in a fleshy, globose, head like cluster. The fruits are large, fleshy, and ovoid. At maturity, they are creamy white and edible, but have an unpleasant taste and odor. The plant is native to Southeast Asia and has spread in early times to a vast area from India to eastern Polynesia. It grows randomly in the wild, and it has been cultivated in plantations and small individual growing plots. The *Morinda citrifolia* flowers are small, white, three to five lobed, tubular, fragrant, and about 1.25 cm long. The flowers develop into compound fruits composed of many small drupes fused into an ovoid, ellipsoid or roundish, lumpy body, with waxy, white, or greenish-white or yellowish, semi-translucent skin. The fruit contains "eyes" on its surface, similar to a potato. The fruit is juicy, bitter, dull-yellow or yellowish-white, and contains numerous red-brown, hard, oblong-triangular, winged 2-celled stones, each containing four seeds. When fully ripe, the fruit has a pronounced odor like rancid cheese. Although the fruit has been eaten by several nationalities as food, the most common use of the *Morinda citrifolia* plant has traditionally been as a red and yellow dye source.

The *Morinda citrifolia* plant is rich in natural ingredients. Those ingredients that have been discovered include from the leaves: alanine, anthraquinones, arginine, ascorbic acid, aspartic acid, calcium, beta carotene, cysteine, cystine, glycine, glutamic acid, glycosides, histidine, iron, leucine, isoleucine, methionine, niacin, phenylalanine, phosphorus, proline, resins, riboflavin, serine, beta sitosterol, thiamine, threonine, tryptophan, tyrosine, ursolic acid, and valine; from the flowers: acacetin 7 o beta d (+) glucopyranoside, 5,7 dimethyl apigenin 4' o beta d(+) galactopyranoside, and 6,8 dimethoxy 3 methylanthraquinone 1 o beta rhamnosyl glucopyranoside; from the fruit: acetic acid, asperuloside, butanoic acid, benzoic acid, benzyl alcohol, 1 butanol, caprylic acid, decanoic acid, (E) 6 dodeceno gamma lactone, (Z,Z,Z) 8,11,14 eicosatrienoic acid, elaidic acid, ethyl decanoate, ethyl hexanoate, ethyl octanoate, ethyl palmitate, (Z) 6 (ethylthiomethyl)benzene, eugenol, glucose, heptanoic acid, 2 heptanone, hexanal, hexanamide, hexanedioic acid, hexanoic acid (hexoic acid), 1 hexanol, 3 hydroxy 2 butanone, lauric acid, limonene, linoleic acid, 2 methylbutanoic acid, 3 methyl 2 buten 1 ol, 3 methyl 3 buten 1 ol, methyl decanoate, methyl elaidate, methyl hexanoate, methyl 3 methylthio propanoate, methyl octanoate, methyl oleate, methyl palmitate, 2 methylpropanoic acid, 3 methylthiopropanoic acid, myristic acid, nonanoic acid, octanoic acid (octoic acid), oleic acid, palmitic acid, potassium, scopoletin, undecanoic acid, (Z,Z) 2,5 undecadien 1 ol, and vomifol; from the roots: anthraquinones, asperuloside (rubichloric acid), damnacanthal, glycosides, morindadiol, morindine, morindone, mucilaginous matter, nor damnacanthal, rubiadin, rubiadin monomethyl ether, resins, soranjidiol, sterols, and trihydroxymethyl anthraquinone monomethyl ether; from the root bark: alizarin, chlororubin, glycosides (pentose, hexose), morindadiol, morindanigrine, morindine, morindone, resinous matter, rubiadin monomethyl ether, and soranjidiol; from the wood: anthragallol 2,3 dimethylether; from the tissue culture: damnacanthal, lucidin, lucidin 3 primeveroside, and morindone 6beta primeveroside; from the plant: alizarin, alizarin alpha methyl ether, anthraquinones, asperuloside, hexanoic acid, morindadiol, morindone, morindogenin, octanoic acid, and ursolic acid.

Processing *Morinda citrifolia* Leaves

The leaves of the *Morinda citrifolia* plant are one possible component of the *Morinda citrifolia* plant that may be present in some compositions of the present invention. For example, some compositions comprise leaf extract and/or leaf juice as described further herein. Some compositions comprise a leaf serum that is comprised of both leaf extract and fruit juice obtained from the *Morinda citrifolia* plant. Some compositions of the present invention comprise leaf serum and/or various leaf extracts as incorporated into a nutraceutical product ("nutraceutical" herein referring to any drug or product designed to improve the health of living organisms such as human beings or mammals).

In some embodiments of the present invention, the *Morinda citrifolia* leaf extracts are obtained using the following process. First, relatively dry leaves from the *Morinda citrifolia* L. plant are collected, cut into small pieces, and placed into a crushing device—preferably a hydraulic press—where the leaf pieces are crushed. In some embodiments, the crushed leaf pieces are then percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments of the present invention, the primary leaf extract is pasteurized to at least partially sterilize the extract and destroy objectionable organisms. The primary leaf extract is pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably via a gas chromatograph containing silicon dioxide and CH2C12-MeOH ingredients using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined with the fruit juice of the fruit of the *Morinda citrifolia* plant to obtain a leaf serum (the process of obtaining the fruit juice to be described further herein). In some embodiments, the leaf serum is packaged and frozen ready for shipment; in others, it is further incorporated into a nutraceutical product as explained herein.

Processing *Morinda citrifolia* Fruit

Some embodiments of the present invention include a composition comprising fruit juice of the *Morinda citrifolia* plant. Because the *Morinda citrifolia* fruit is for all practical purposes inedible, the fruit must be processed in order to make it palatable for human consumption and included in the compositions of the present invention. Processed *Morinda citrifolia* fruit juice can be prepared by separating seeds and peels from the juice and pulp of a ripened *Morinda citrifolia* fruit; filtering the pulp from the juice; and packaging the juice. Alternatively, rather than packaging the juice, the juice can be immediately included as an ingredient in another product, frozen or pasteurized. In some embodiments of the present invention, the juice and pulp can be pureed into a homogenous blend to be mixed with other ingredients. Other processes include freeze drying the fruit and juice. The fruit and juice can be reconstituted during production of the final juice product. Still other processes may include air drying the fruit and juices prior to being masticated.

In a currently preferred process of producing *Morinda citrifolia* fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, but preferably for 2 to 3 days. The fruit is ripened or aged by being placed on equipment so that the fruit does not contact the ground. The fruit is preferably covered with a cloth or netting material during aging, but the fruit can be aged without being covered. When ready for further processing the fruit is light in color, such as a light green, light yellow, white or translucent color. The fruit is inspected for spoilage or for excessive green color and firmness. Spoiled and hard green fruit is separated from the acceptable fruit.

The ripened and aged fruit is preferably placed in plastic lined containers for further processing and transport. The containers of aged fruit can be held from 0 to 30 days, but preferably the fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The *Morinda citrifolia* juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.). Another product manufactured is *Morinda citrifolia* puree and puree juice, in either concentrate or diluted form. Puree is essentially the pulp separated from the seeds and is different than the fruit juice product described herein.

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, a reverse osmosis filtration device, and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The resulting pulp extract typically has a fiber content of 10 to 40 percent by weight. The resulting pulp extract is preferably pasteurized at a temperature of 181° F. (83° C.) minimum and then packed in drums for further processing or made into a high fiber product.

Processing *Morinda citrifolia* Seeds

Some *Morinda citrifolia* compositions of the present invention include seeds from the *Morinda citrifolia* plant. In some embodiments of the present invention, *Morinda citrifolia* seeds are processed by pulverizing them into a seed powder in a laboratory mill. In some embodiments, the seed powder is left untreated. In some embodiments, the seed powder is further defatted by soaking and stirring the powder in hexane—preferably for 1 hour at room temperature (Drug: Hexane—Ratio 1:10). The residue, in some embodiments, is then filtered under vacuum, defatted again (preferably for 30 minutes under the same conditions), and filtered under vacuum again. The powder may be kept overnight in a fume hood in order to remove the residual hexane.

Still further, in some embodiments of the present invention, the defatted and/or untreated powder is extracted, preferably with ethanol 50% (m/m) for 24 hours at room temperature at a drug solvent ratio of 1:2.

Processing *Morinda citrifolia* Oil

Some embodiments of the present invention may comprise oil extracted from the *Morinda Citrifolia* plant. The method for extracting and processing the oil is described in U.S. patent application Ser. No. 09/384,785, filed on Aug. 27, 1999 and issued as U.S. Pat. No. 6,214,351 on Apr. 10, 2001, which is incorporated by reference herein. The *Morinda citrifolia* oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

Compositions and Their Use

This invention relates to a method and composition for providing in various health benefits by administering various bioactive compounds derived from the plant *Morinda cirtrifolia* to individuals. This invention relates to using one or more of the following: Noni Leaf Extract; Noni Leaf Juice; and/or Roast Leaf to inhibit the following: HMG-CoA Reductase; Phosphodiesterases (3 and 4) PDE3 and PDE4; 5-Lipoxygenase (LOX) and 15-LOX; Xanthine Oxidase (X0); Gamma Amino Butyric Acid (GABA) and the growth of the second most common human skin cancer cell line. More particularly this invention relates to administering one or more of the following: Pyro-phorbide a, Pheophorbide a, Purpin 7, and/or Pheophorbide Phypolesper all which may be derived from Noni leaf extract, Noni leaf juice, and/or Roast leaf. Moreover, the foregoing formulations result in alleviating pain and inflammation.

Compositions of the present invention may comprise any of a number of *Morinda citrifolia* components such as: leaf extract, leaf juice, leaf serum, fruit juice, fruit pulp, pulp extract, puree, seeds (whether defatted or untreated), and oil. Compositions of the present invention may also include various other ingredients. Examples of other ingredients include, but are not limited to: artificial flavoring, other natural juices or juice concentrates such as a natural grape juice concentrate or a natural blueberry juice concentrate; carrier ingredients; and others as will be further explained herein.

Any compositions having the leaf extract from the *Morinda citrifolia* leaves, may comprise one or more of the following: the primary leaf extract, the hexane fraction, methanol fraction, the secondary hexane and methanol fractions, the leaf serum, or the nutraceutical leaf product.

In some embodiments of the present invention, active ingredients or compounds of *Morinda citrifolia* components may be extracted out using various procedures and processes commonly known in the art. For instance, the active ingredients may be isolated and extracted out using alcohol or alcohol-based solutions, such as methanol, ethanol, and ethyl acetate, and other alcohol-based derivatives using methods known in the art. These active ingredients or compounds may be isolated and further fractioned or separated from one another into their constituent parts. Preferably, the compounds are separated or fractioned to identify and isolate any active ingredients that might help to prevent disease, enhance health, or perform other similar functions. In addition, the compounds may be fractioned or separated into their constituent parts to identify and isolate any critical or dependent interactions that might provide the same health-benefiting functions just mentioned.

Any components and compositions of *Morinda citrifolia* may be further incorporated into a nutraceutical product (again, "nutraceutical" herein referring to any drug or product designed to improve the health of living organisms such as human beings or mammals). Examples of nutraceutical products may include, but are not limited to: intravenous products, topical dermal products, wound healing products, skin care products, hair care products, beauty and cosmetic products (e.g., makeup, lotions, etc.), burn healing and treatment products, first-aid products, antibacterial products, lip balms and ointments, bone healing and treatment products, meat tenderizing products, anti-inflammatory products, eye drops, deodorants, antifungal products, arthritis treatment products, muscle relaxers, toothpaste, and various nutraceutical and other products as may be further discussed herein.

The compositions of the present invention may be formulated into any of a variety of embodiments, including oral compositions, topical dermal solutions, intravenous solutions, and other products or compositions.

Oral compositions may take the form of, for example, tablets, lozenges, aqueous or oily suspensions, dispersible powders or granules, emulsions, syrups, or elixirs. Compositions intended for oral use may be prepared according to any method known in the art, and such compositions may contain one or more agents such as sweetening agents, flavoring agents, coloring agents, and preserving agents. They may also contain one or more additional ingredients such as vitamins and minerals, etc. Tablets may be manufactured to contain one or more *Morinda citrifolia* components in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Aqueous suspensions may be manufactured to contain the *Morinda citrifolia* components in admixture with excipients suitable for the manufacture of aqueous suspensions. Examples of such excipients include, but are not limited to: suspending agents such as sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide like lecithin, or condensation products of an alkylene oxide with fatty acids such as polyoxyethylene stearate, or condensation products of ethylene oxide with long chain aliphatic alcohols such as heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides such as polyethylene sorbitan monooleate.

Typical sweetening agents may include, but are not limited to: natural sugars derived from corn, sugar beets, sugar cane, potatoes, tapioca, or other starch-containing sources that can be chemically or enzymatically converted to crystalline chunks, powders, and/or syrups. Also, sweeteners can comprise artificial or high-intensity sweeteners, some of which may include aspartame, sucralose, stevia, saccharin, etc. The concentration of sweeteners may be between from 0 to 50 percent by weight of the *Morinda citrifolia* composition, and more preferably between about 1 and 5 percent by weight.

Typical flavoring agents can include, but are not limited to, artificial and/or natural flavoring ingredients that contribute to palatability. The concentration of flavors may range, for example, from 0 to 15 percent by weight of the *Morinda citrifolia* composition. Coloring agents may include food-grade artificial or natural coloring agents having a concentration ranging from 0 to 10 percent by weight of the *Morinda citrifolia* composition.

Typical nutritional ingredients may include vitamins, minerals, trace elements, herbs, botanical extracts, bioactive chemicals, and compounds at concentrations from 0 to 10 percent by weight of the *Morinda citrifolia* composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, chlorella powder, Dong Quai powder, Ecchinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The ingredients to be utilized in a topical dermal product may include any that are safe for internalizing into the body of a mammal and may exist in various forms, such as gels, lotions, creams, ointments, etc., each comprising one or more carrier agents. The ingredients or carrier agents incorporated into systemically (e.g., intravenously) administered compositions may also comprise any known in the art.

In one exemplary embodiment, a *Morinda citrifolia* composition of the present invention comprises one or more of a processed *Morinda citrifolia* component present in an amount by weight between about 0.01 and 100 percent by weight, and preferably between 0.01 and 95 percent by weight. Several embodiments of formulations are included in U.S. Pat. No. 6,214,351, issued on Apr. 10, 2001. However, these compositions are only intended to be exemplary, as one ordinarily skilled in the art will recognize other formulations or compositions comprising the processed *Morinda citrifolia* product.

In another exemplary embodiment, the internal composition comprises the ingredients of: processed *Morinda citrifolia* fruit juice or puree juice present in an amount by weight between about 0.1-80 percent; processed *Morinda citrifolia* oil present in an amount by weight between about 0.1-20 percent; and a carrier medium present in an amount by weight between about 20-90 percent. *Morinda citrifolia* puree juice or fruit juice may also be formulated with a processed *Morinda citrifolia* dietary fiber product present in similar concentrations.

EXAMPLES

The following examples illustrate some of the embodiments of the invention. These examples are not intended to be limiting in any way, but are merely illustrative of benefits, advantages, and remedial effects of some embodiments of the *Morinda citrifolia* compositions of the present invention.

Example 1

Noni Leaf Juice

In one example, the effects of *Morinda Citrifolia* leaf juice on 5-LOX and 15-LOX, HMG-CoA, PDE3 and PDE4, XO and GABA were studied. *Morinda Citrifolia* leaf juice was administered to rabbits, rats, humans and bovines at various concentration dosages. Inhibition of 5-LOX and 15-LOX was observed in both rabbits and humans, respectively. Inhibition of HMG-CoA Reductase was observed in rats. Inhibition of PDEs was observed in humans. Inhibition of xanthine oxidase was observed in bovines and inhibition of GABA was observed in rats. The following tables summarize the results of these studies.

TABLE 1

Example 1

| Enzyme | Test Animal | No. Samples | % Inhibition | Std. Deviation |
|---|---|---|---|---|
| HMG-CoA Reductase | Rat | 2 | 10% | 29 |
|  |  | 2 | 5% | 5 |
|  |  | 2 | 1% | −3 |
| Lipoxygenase 15-LOX | Rabbit | 2 | 10% | 111 |
|  |  | 2 | 5% | 102 |
|  |  | 2 | 1% | 87 |
| Lipoxygenase 5-LOX | Human | 2 | 10% | 101 |
|  |  | 2 | 5% | 85 |
|  |  | 2 | 1% | 41 |
| Phosphodiesterase PDE3 | Human | 2 | 10% | 71 |
|  |  | 2 | 5% | 33 |
|  |  | 2 | 1% | 8 |
| Phosphodiesterase PDE4 | Human | 2 | 10% | 94 |
|  |  | 2 | 5% | 45 |
|  |  | 2 | 1% | 17 |
| Phosphodiesterase PDE5 | Human | 2 | 10% | 41 |
|  |  | 2 | 5% | 0 |
|  |  | 2 | 1% | 6 |
| Xanthine Oxidase | Bovine | 2 | 10% | 33 |
|  |  | 2 | 5% | 29 |
|  |  | 2 | 1% | 6 |
| $GABA_2$, Agonist Site | Rat | 2 | 10% | 105 |
|  |  | 2 | 5% | 104 |
|  |  | 2 | 1% | 103 |

Example 2

Noni Leaf Extract

TABLE 2

Example 2

| | Test Animal | No. Samples | % NLEX in Solution | % Inhibition |
|---|---|---|---|---|
| HMG-CoA Reductase | | | | |
| NLEX-P | rat | 2 | 0.1% | 54 |
|  |  | 2 | 0.05% | 40 |
|  |  |  | 0.025% | 7 |
| Phophodiestrerase PDE3 | | | | |
| NLEX-P | hum | 2 | 0.1% | 79 |
|  |  | 2 | 0.05% | 69 |
|  |  | 2 | 0.025% | 58 |
| Phophodiestrerase PDE4 | | | | |
| NLEX-P | hum | 2 | 0.1% | 82 |
|  |  | 2 | 0.5% | 69 |
|  |  | 2 | 0.025% | 54 |
| Phophodiestrerase PDE5 | | | | |
| NLEX-P | hum | 2 | 0.1% | 87 |
|  |  | 2 | 0.05% | 84 |
|  |  | 2 | 0.025% | 77 |

Example 2 (above) was based on the following parameters:

TABLE 3

| HMG-CoA Reductase | |
|---|---|
| Source: | Wistar Rat liver |
| Substrate: | 2.504[14C]HMG-CoA |
| Vehicle: | 1% DMSO |
| Pre-Incubation Time/Temp: | 15 minutes @ 37° C. |
| Incubation Buffer: | 100 mM Potassium Phosphate, pH 7.5, 20 mM G-6-P. 2.5 mM NADP 10 mM EDTA 5 mM DTT, 14 U G-6-P-DH |
| Quantitation Method: | Quantitation of [14C]Mevalonate |
| Significance Criteria: | >50% of max stimulation or inhibition |

TABLE 4

| Phosphodiesterase PDE3 | |
|---|---|
| Source: | Human platelets |
| Substrate: | 1.01/.2M (PH]cAMP + cAMP) |
| Vehicle: | 1% DMSO |
| Pre-Incubation Time/Temp: | 15 minutes @ 25° C. |
| Incubation Time/Temp: | 20 minutes @ 25° C. |
| Incubation Buffer: | 50 mM Tris-HCL, pH 7.5.5 mM MgC12 |
| Quantitation Method: | Quantitation of (PH) Adenosine |
| Significance Criteria: | ≧50% of max stimulation or inhibition |

TABLE 5

| Phosphodiesterase PDE4 | |
|---|---|
| Source: | Human U937 cells |
| Substrate: | 1.01 MM (PHicAMP + cAMP) |
| Vehicle: | 1% DMSO |
| Pre-Incubation Time/Temp: | 15 minutes @ 25° C. |
| Incubation Time/Temp: | 20 minutes @ 25° C. |
| Incubation Buffer: | 50 mM Tris-HCL, pH 7.5.5 mM MgC12 |
| Quantitation Method: | Quantitation of (PH) Adenosine |
| Significance Criteria: | ≧50% of max stimulation or inhibition |

TABLE 6

| Phosphodiesterase PDE5 | |
|---|---|
| Source: | Human platelets |
| Substrate: | 1.01/zM (PH]cGMP + cGMP) |
| Vehicle: | 1% DMSO |
| Pre-Incubation Time/Temp: | 15 minutes @ 25° C. |
| Incubation Time/Temp: | 20 minutes @ 25° C. |
| Incubation Buffer: | 50 mM Tris-HCL, pH 7.5.5 mM MgC12 |
| Quantitation Method: | Quantitation of (PH) Guanosine |
| Significance Criteria: | >50% of max stimulation or inhibition |

Example 3

In this next example, *Morinda citrifolia* leaf juice and leaf extract was shown to significantly inhibit the growth of the second most common type of human skin cancer. In this example, assays were performed to detect changes in cell proliferation based on the ability of viable cells to cause alamarBlue to change from non-fluorescent blue to a reduced, fluorescent red form. With the results obtained from the alamarBlue reaction, cell proliferation can be quantified and metabolic activity of viable cells can be examined. Test compounds including *Morinda citrifolia* leaf extract, leaf juice, and roast leaf were tested for their effects on the proliferation of human epidermoid carcinoma cell line-A431 at assay concentrations from 0.01 to 100 μg/ml or 0.0001% to 1% through serial 10-fold dilutions.

In summary, it was found that the leaf extract at concentrations between 10 and 100 μg/ml, as well as the leaf juice between 0.1% and 1%, caused significant growth inhibition (<50% of growth) relative to the vehicle-treated control in the tumor cell line—whereas the roast leaf failed to show a significant effect (0.01-100 μg/ml). Significant inhibitory activity was also observed for the concurrently tested standard reference agent, Mitomycin, at <10 p.M. Consequently, semi-quantitative determinations of estimated $LC_{50}$ (50% inhibition concentration), TGI (total growth inhibition) and $LC_{50}$ (50% lethal concentration) by nonlinear regression analysis were calculated. Following is a description of the materials, equipment, and methods used in the assay, as well as tables summarizing the results.

Test Substances and Concentrations.

*Morinda citrifolia* leaf extract, leaf juice, and roast leaf were provided by Tahitian Noni International, Inc. for in vitro anti-tumor studies. The *Morinda citrifolia* compounds were dissolved in sterile distilled water and then diluted with sterile distilled water to obtain initial working solutions of 10000, 1000, 100, 10, and 1 μg/ml for the leaf extract and roast leaf, as well as 100, 10, 1, 0.1 and 0.01% for the leaf juice. In testing, 100-fold dilution was made in culture media to get final assay concentrations of 100, 10, 1, 0.1 and 0.01 μg/ml, and 1, 0.1, 0.01, 0.001 and 0.0001%, respectively.

Cell Line and Culture Media.

The tumor cell line, A431 (human epidermoid carcinoma), obtained from American Type Culture Collection (ATCC CRL-1555), was incubated in an air atmosphere of 5% $CO_2$ at 37° C. The culture medium was used with Dulbecco's Modified Eagle's medium, 90%; Fetal Bovine Serum, 10% and supplemented with 1% Antibiotic-Antimycotic.

Chemicals.

The following chemicals were used in the assay: Alamar-Blue (Biosource, USA), Antibiotic-Antimycotic (GIBCO BRL, USA), Dulbecco's Modified Eagle's Medium (GIBCO BRL, USA), Fetal Bovine Serum (HyClone, USA), and Mitomycin (Kyowa, Japan).

Equipment.

The following equipment was used in the assay: $CO_2$ Incubator (Form a Scientific Inc., USA), Centrifuge 5810R (Eppendorf, Germany), Hemacytometer (Hausser Scientific Horsham, USA), Inverted Microscope CK-40 (Olympus, Japan), System Microscope E-400 (Nikon, Japan), Spectrafluor Plus (Tecan, Austria), and Vertical Laminar Flow (Tsao Hsin, R.O.C.).

Methods.

The anti-proliferation for the test substances was evaluated. Aliquots of 100 pl of cell suspension (about $3 \times 10^3$/well) were placed in 96-well microtiter plates in an atmosphere of 5% $CO_2$ at 37° C. After 24 hours, 100 pl of growth medium and 2 pl of test solution, Mitomycin or vehicle (distilled water) were added respectively per well in duplicate for an additional 72-hour incubation. Two test compounds, leaf extract and roast leaf, were evaluated at concentrations of 100, 10, 1, 0.1 and 0.01 pg/ml. The other compound, leaf juice, was evaluated at concentrations of 1, 0.1, 0.01, 0.001 and 0.0001%. At the end of incubation, 20 pl of 90% alamar-Blue reagent was added to each well for another 6-hour incubation before detection of cell viability by fluorescent intensity. Fluorescent intensity was measured using a Spectrafluor Plus plate reader with excitation at 530 nm and demission at 590 nm.

$IC_{50}$, TGI, and $LC_{50}$ values were then determined. $IC_{50}$ (50% Inhibition Concentration) is the test compound concentration where the increase from $time_o$ in the number or mass of treated cells was only 50% as much as the corresponding increase in the vehicle-control at the end of the experiment. TGI (Total Growth Inhibition) is the test compound concentration where the number or mass of treated cells at the end of the experiment was equal to that at $time_0$. $LC_{50}$ (50% Lethal Concentration) is the test compound concentration where the number or mass of treated cells at the end of the experiment was half that at $time_0$. The measured results were calculated by the following formula:

$$PG(\%) = 100 \times (\text{Mean } F_{test} - \text{Mean } F_{time0}) / (\text{Mean } F_{ctr} - \text{Mean } F_{time0})$$

If $(\text{Mean } F_{test} - \text{Mean } F_{time0})^{<0}$, then $$PG(\%) = 100 \times (\text{Mean } F_{test} - \text{Mean } F_{time0}) / (\text{Mean } F_{time0} - \text{Mean } F_{blank})$$

Where: PG=percent growth; Mean $F_{time0}$=The average of 2 measured fluorescent intensities of reduced alamarBlue at the time just before exposure of cells to the test substance; Mean $F_{test}$=The average of 2 measured fluorescent intensities of alamarBlue after 72-hour exposure of cells to the test substance; Mean $F_{ctrl}$=The average of 2 measured fluorescent intensities of alamarBlue after 72-hour incubation without the test substance; and Mean $F_{blank}$=The average of 2 measured fluorescent intensities of alamarBlue in medium without cells after 72-hour incubation.

A decrease of 50% or more ($\geq 50\%$) in fluorescent intensity relative to the vehicle-treated control indicated significant cell growth inhibition, cytostatic or cytotoxic activity, and a semi-quantitative $IC_{50}$, TGI, and $LC_{50}$ were then determined by nonlinear regression using GraphPad Prism (GraphPad Software, USA).

Results.

The following tables summarize the results of the assay.

Effect of *Morinda Citrifolia* Test Substances on the Growth of A431 Skin Tumor Cells

TABLE 7

| Test Substance | Assay Name | A Blank | Time 0 | "Vehicle | Percent Grown (Mean = SEM, n = 2) Concentration (111/ml) | | | | |
|---|---|---|---|---|---|---|---|---|---|
| | | | | | 100 | 10 | 1 | 0.1 | 0.01 |
| Leaf Extract | Skin | −100 | 0 | 100 | 46 +/− 1 | 72 +/− 5 | 89 +/− 1 | 88 +/− 3 | 101 +/− 7 |
| Roast Leaf | Skin | −100 | 0 | 100 | 72 +/− 5 | 79 +/− 4 | 87 +/− 2 | 91 +/− 6 | 99 +/− 5 |

TABLE 8

| Test Substance | Assay Name | Blank | Time 0 | Vehicle | Percent Grown Concentration (%) | | | | |
|---|---|---|---|---|---|---|---|---|---|
| | | | | | 1 | 0.1 | 0.01 | 0.001 | 0.001 |
| Leaf Juice | Skin | −100 | 0 | 100 | 74 +/− 2 | 83 +/− 2 | 77 +/− 2 | 83 +/− 2 | 94 +/− 1 |
| Roast Leaf | Skin | −100 | 0 | 100 | 72 +/− 5 | 79 +/− 4 | 87 +/− 2 | 91 +/− 6 | 94 +/− 5 |

TABLE 9

| Test Substance | Assay Name | Blank | Time 0 | Vehicle | Percent Grown Concentration (ttM) | | | | |
|---|---|---|---|---|---|---|---|---|---|
| | | | | | 10 | 1 | 0.1 | 0.01 | 0.001 |
| Mitomycin | Skin | −100 | 0 | 100 | 97 +/− 0 | 35 +/− 8 | 7 +/− 3 | 82 +/− 3 | 101 +/− 5 |

A decrease of 50% or more (≧50%) in fluorescent intensity relative to vehicle-treated control indicates significant growth inhibition, cytostatic or cytotoxic activity.

As utilized in tables 7-10, the following terms mean:

Blank: In duplicate, average fluorescent intensity of alamar-Blue in medium without cells after 3-day incubation period relative to $time_d$ (transformed and recorded as −100%).

$Time_0$: In duplicate, average fluorescent intensity of alamar-Blue in medium just before exposure of cells to test substance (transformed and recorded as 0%).

Vehicle: In duplicate, average fluorescent intensity of alamar-Blue in medium containing cells and added vehicle after 3-day incubation period relative to $time_d$ (transformed and recorded as 100%).

Mso (50% Inhibition Concentration): Test compound concentration where the increase from $time_d$ in the number or mass of treated cells was only 50% as much as the corresponding increase in the vehicle-control at the end of experiment.

TGI (Total Growth Inhibition): Test compound concentration where the number or mass of treated cells at the end of experiment was equal to that at timed.

$LC_{50}$ (50% Lethal Concentration): Test compound concentration where the number or mass of treated cells at the end of experiment was half that at timed.

The following figures are concentration-response curves for inhibition of growth in A431 human tumor cell line treated with Leaf Extract, Leaf Juice and Roast Leaf.

$IC_{50}$ $TG_1$ and $LC_{50}$ Values of *Morinda Citrifolia* Test Compounds

TABLE 10

| Compound | Assay Name | aic50 | bTGI | cl__, Cso |
|---|---|---|---|---|
| Leaf Extract | Tumor, Skin | 76 μg/ml | >100 μg/ml | >100 μg/ml |
| Leaf Juice | Tumor, Skin | 0.20% | 0.36% | 0.65% |
| Roast Leaf | Tumor, Skin | >100 μg/ml | >100 μg/ml | >100 μg/ml |
| Mitomycin | Tumor, Skin | 0.035 μM | 0.19 μM | 1.0 μIVI |

A semi-quantitative determination of $IC_{50}$ $TG_1$ and $LC_{50}$ was carried out by nonlinear regression analysis using Graph-Pad Prism (GraphPad Software, USA).

In summary, some embodiments of the present invention provide using Noni leaf juice and Noni leaf extract to inhibit: HMG-CoA Reductase; PDE3 and PDE4; 5-LOX and 15-LOX; XO; GABA and the growth of the second most common human skin cancer cell line, for the purpose of: alleviating pain and inflammation; treating prostate cancers; lower cholesterol levels; counteracting Diabetes Type II; maintaining the highest possible integrity of cellular interactions in the brain resulting in an undisturbed neural function, (i.e. neuroprotection); ameliorating the effects of asthma and allergies; improving energy; improving insulin secretion; decreasing kidney stone accumulation; alleviating the effects of gout; minimizing convulsions related to epilepsy and other seizure disorders; and providing palliative effects to those addicted to drugs.

Example 4

Additionally, the squeezed juice from fresh *Morinda citrifolia* leaf was utilized to identify by bio-assay on Adenosine A2A four bio-active compounds which have been isolated and identified to have significant bioactivity. Their structures have been determined by NMR techniques and mass spectrometry and they have been identified as Pyro-phorbide a, Pheoporbide a, Purpin 7, and Pheophorbide Phytolester. The isolation and characterization of the above referenced bioactive compounds provides a significant explanation for the anti-inflammatory and analgesic properties of extracts derived from the *Morinda citrifolia* plant, particularly from the leaf of the plant.

The present invention may be embodied in other specific forms without departing from its spirit of essential characteristics. The described embodiments are to be considered in all respects only as illustrative and not restrictive. The scope of the invention is, therefore, indicated by the appended claims, rather than by the foregoing description. All changes that come within the meaning and range of equivalency of the claims are to be embraced within their scope.

What is claimed is:

1. A method of treating inflammation in a mammal, which comprises:
   acquiring *Morinda citrifolia* leaves;
   cutting the leaves into small pieces;
   placing the leaves into a crushing device;
   crushing the leaves;
   percolating the leaf pieces in an alcohol solution;
   collecting the alcohol and all alcohol soluble ingredients from the alcohol leaf slurry;
   allowing the alcohol to evaporate leaving a primary leaf extract;
   dissolving the leaf extract in water; and administering the diluted leaf extract to a mammal to decrease or prevent inflammation and/or pain.

2. The method of claim 1, wherein the leaf extract is dissolved in water to dilute the solution by an amount selected from a list consisting of:

10,000 milligrams per milliliter, 1000 milligrams per milliliter 100 milligrams per milliliter, 10 milligrams per milliliter, 1 milligram per milliliter, 0.1 milligrams per milliliter, 0.001 milligrams per milliliter, and 0.0001 milligrams per milliliter.

3. The method of claim 1, wherein the primary leaf extract is pasteurized.

4. The method of claim 1, wherein the primary leaf extract is partially sterilized.

5. The method of claim 1, further comprising a step of placing the primary leaf extract in a centrifuge to remove any remaining leaf juice and other materials, including chlorophyll.

6. The method of claim 1, wherein the primary leaf extract is further fractionated into a secondary fraction selected from a list consisting of:

a dry hexane fraction; and an aqueous methanol fraction.

7. The method of claim 6, wherein the secondary fractions are produced utilizing a gas chromatograph containing silicone dioxide.

8. The method of claim 6, further comprising the steps of dividing the secondary methanol fraction into additional methanol fractions.

9. The method of claim 6, wherein the secondary hexane fraction is further fractionated into additional hexane fractions.

10. The method of claim 1, further comprising a step of combining the leaf extract with the fruit juice of the fruit of the *Morinda citrifolia* plant to obtain a leaf serum.

11. The method of claim 2, further comprising the step of combining the primary extract with a carrier medium prior to administration.

12. The method of claim 1, wherein the diluted leaf extract to administered to the mammal to selectively inhabit Cyclooxygenase-2 relative to Cyclooxygenase-1.

13. The method of claim 1, wherein the decreasing or prevention of inflammation and/or pain is accomplished while maintaining gastric mucosal integrity.

14. The method of claim 1, further comprising the step of diluting the dissolved extract by 100-fold prior to administration.

15. The method of claim 1, wherein said active ingredient is selected from a list consisting of Pyro-phorbide a, Pheoporbide a, Purpin 7, and Pheophorbide Phytolester.

* * * * *